(12) United States Patent
Sode

(10) Patent No.: US 7,244,581 B2
(45) Date of Patent: Jul. 17, 2007

(54) GLUCOSE DEHYDROGENASE

(76) Inventor: Koji Sode, 1-13-16, Minami, Meguro-Ku, Tokyo 152-0013 (JP)

( * ) Notice: Subject to any disclaimer, the term of this patent is extended or adjusted under 35 U.S.C. 154(b) by 0 days.

(21) Appl. No.: 10/517,702

(22) PCT Filed: Jun. 13, 2003

(86) PCT No.: PCT/JP03/07542

§ 371 (c)(1),
(2), (4) Date: Aug. 2, 2005

(87) PCT Pub. No.: WO03/106668

PCT Pub. Date: Dec. 24, 2003

(65) Prior Publication Data

US 2006/0073580 A1    Apr. 6, 2006

(30) Foreign Application Priority Data

Jun. 13, 2002  (JP) .......................... 2002-172955
Mar. 17, 2003  (JP) .......................... 2003-071744

(51) Int. Cl.
*C12Q 1/54*   (2006.01)
*C12P 21/06*  (2006.01)
*C07H 21/04*  (2006.01)
*C12N 9/02*   (2006.01)

(52) U.S. Cl. .................. 435/14; 435/69.1; 435/252.31; 435/471; 435/190; 435/26; 435/189; 536/23.2

(58) Field of Classification Search .................. None
See application file for complete search history.

(56) References Cited

U.S. PATENT DOCUMENTS 6,562,958 B1 *   5/2003   Breton et al. .............. 536/23.7

FOREIGN PATENT DOCUMENTS

| EP | 1 167 519 A1 | 1/2002 |
| EP | 1 367 120 A | 12/2003 |
| JP | 2001-346587 A | 12/2001 |

OTHER PUBLICATIONS

Yoshida et al Enz & mol Tech, 2002, 30, 312-318.*
English language abstract of Hiroshi Hayade et al., "CSJ: The Chemical Society of Japan Dai 79 Shunki Nenkai—Koen Yokoshu II", CSJ: The Chemical Society of Japan, Mar. 15, 2001, p. 897.
Cleton-Jansen A-M et al., "Glucose dehydrogenase-B Pyrroloquinoline-quinone Presursor (EC 1.1.99.17)" Swiss-Prot, Oct. 16, 2001 XP002203013.
Hiroshi Hayade et al., "CSJ: The Chemical Society of Japan Dai 79 Shunki Nenkai—Koen Yokoshu II", CSJ: The Chemical Society of Japan, Mar. 15, 2001, p. 897.
A. Oubrie et al., "Structure and mechanism of soluble quinoprotein glucose dehydrogenase", EMBO J., 1999, vol. 18, No. 19, p. 5187-94.
A. Oubrie et al., "The 1.7 A crystal structure of the apo from of the soluble quinoprotein glucose dehydrogenase from Acinetobacter calcoaceticus reveals a novel internal conserved sequence repeat", J. Mol. Biol., 1999, vol. 289, No. 2, p. 319-33.

* cited by examiner

*Primary Examiner*—Rebecca E. Prouty
*Assistant Examiner*—M. Y. Meah
(74) *Attorney, Agent, or Firm*—Birch, Stewart, Kolasch & Birch, LLP

(57) ABSTRACT

Disclosed is a modified glucose dehydrogenase having pyrroloquinoline quinone as a coenzyme, wherein one or more amino acid residues in a region of amino acid 349-377 of water-soluble PQQGDH derived from *Acinetobacter calcoaceticus* is replaced with other amino acid residues and has an inhibition constant (Ksi) of 200 mM or more. The modified water-soluble PQQGDH of the invention can be utilized for measuring glucose levels in the presence of high concentrations of glucose because of the low substrate inhibition by glucose.

7 Claims, 4 Drawing Sheets

GLUCOSE DEHYDROGENASE

TECHNICAL FIELD

The present invention relates to a modified glucose dehydrogenase (GDH), which is an enzyme having pyrroloquinoline quinone (PQQ) as a coenzyme, wherein certain amino acids are replaced with other amino acids. The modified enzyme of the invention is useful in the quantification of glucose for use in clinical diagnosis and food analysis.

BACKGROUND OF THE INVENTION

Glucose concentration is an important indicator in clinical diagnosis as an important marker for diabates. In addition, quantification of glucose concentration is an important indicator for monitoring the process of fermentation production using bacteria. Conventionally, quantification of glucose has been performed by enzymatic methods using glucose oxidase (GOD) or glucose-6-phosphate dehydrogenase (G6PDH). These days, the use of glucose dehydrogenase having pyrroloquinoline quinone as a coenzyme (PQQGDH) is attracting attention in glucose quantification. PQQGDH has highly oxidative activity towards glucose and it does not require oxygen as an electron acceptor since PQQGDH bears its coenzyme. Thus PQQGDH is a promising enzyme to be applied on glucose assays, for example, as a recognition devise of a glucose sensor.

PQQGDH is a glucose dehydrogenase having pyrroloquinoline quinone as a coenzyme, and catalyzes the reaction of oxidizing glucose to produce gluconolactone. Two types of PQQGDHs are known: membrane-bound and water-soluble. Membrane-bound PQQGDH is a single-peptide protein with an approximate molecular weight of 87 kDa, and is found in a wide variety of gram-negative bacteria. On the other hand, water-soluble PQQGDH has been found in some strains of *Acinetobacter calcoaceticus* (Biosci. Biotech. Biochem. (1995), 59 (8), 1548–1555), and its structural gene has been cloned and its amino acid sequence determined (Mol. Gen. Genet. (1989), 217:430–436). Water-soluble PQQGDH derived from *A. calcoaceticus* is a water-soluble homodimer enzyme consisting of two 50 kDa subunits. It requires PQQ and $Ca^{2+}$ for its activity and shows the enzyme activity of as high as 2200 U/mg–7400 U/mg. Isoelectric points are approximately 9.2 and 10.2 for apoenzyme without bound PQQ and holoenzyme, respectively, indicating that the enzyme is a basic protein (K. Matsushita, et al. (1995) Biosci. Biotech. Biochem., 59, 1548–1555). In addition, the results of X-ray structural analysis of water-soluble PQQGDH have been published and reveal the conformation of water-soluble PQQGDH and estimated location of PQQ and $Ca^{2+}$ (A. Oubrie, et al. (1999) J. Mol. Bio., 289, 319–333, A. Oubrie, et al. (1999) The EMBO Journal, 18 (19), 5187–5194, and A. Oubrie, et al. (1999), PNAS 96 (21), 11787–11791).

The wild type water-soluble PQQGDH shows a marked reduction in its activity by substrate inhibition under the glucose concentration of 100 mM or more. For this reason, quantitative measurement of the substrate concentration is difficult under high substrate concentration. The mechanism of substrate inhibition is not yet known.

Hence, the present invention is aimed at providing a modified water-soluble PQQGDH which shows a little reduction of enzyme activity due to substrate inhibition.

DISCLOSURE OF THE INVENTION

As a result of extensive research to modify the conventional water-soluble PQQGDH to develop a PQQGDH capable of quantifying glucose even at high glucose concentrations, the inventor successfully obtained an enzyme with less substrate inhibition by introducing amino acid mutations at certain regions of water-soluble PQQGDH.

The present invention relates to a glucose dehydrogenase having pyrroloquinoline quinone as a coenzyme, wherein one or more amino acids in the amino acids residues 349–377 of water-soluble PQQGDH derived from *Acinetobacter calcoaceticus* are replaced with other amino acids, and having an inhibition constant (Ksi) of 200 mM or more.

As used herein, the inhibition constant (Ksi) means the higher one of the substrate concentrations exhibiting half the maximum enzyme activity observed. Under the conditions in which substrate inhibition in enzyme activity can be observed, inhibition constant means an enzyme-specific value determined by the following formula:

$$V=V\mathrm{max}/[1+(Km/S)+(S/K'si)]$$

wherein V is reaction rate; Vmax is the maximum reaction rate; Km is Michaelis-Menten constant; S is substrate concentration; K' si is a theoretical value of the inhibition constant. The higher the K' si value is, the higher the substrate concentration at which substrate inhibition is observed will be, and substrate inhibition will be alleviated. Since it is difficult to measure K' si accurately in the presence of impurities, the observational Ksi value described above is used herein.

Although not intended to be bound by a specific theory, the amino acid region 349–377 is predicted to be involved in the interaction the substrate glucose, because this region corresponds to the region forming the 4D5A loop according to the topological prediction based upon PQQGD conformation revealed by A. Oubrie et al.

In this specification, the term "correspond" with reference to amino acid residues or regions means that some amino acid residues or regions have an equivalent function in two or more proteins which are structurally similar but not identical. For example, a certain region in water-soluble PQQGDH derived from organisms other than *Acinetobacter calcoaceticus* is said to "correspond to the region of amino acid residues 349–377 of water-soluble PQQGDH derived from *Acinetobacter calcoaceticus*" when the amino acid sequence of such a region has a high similarity to the amino acid sequence in the 349–377 region of water-soluble PQQGDH derived from *Acinetobacter calcoaceticus*, and the same function can be reasonably predicted based on the secondary structure of the relevant regions in the proteins. Additionally, the amino acid residue 17 of the relevant region is said to "correspond to the amino acid residue 365 of water-soluble PQQGDH derived from *Acinetobacter calcoaceticus*". The amino acid numbering in this specification starts from the initiator methionine as the +1 position.

Preferably, in the glucose dehydrogenase of the present invention, at least one amino acid residues selected from the group consisting of Met365, Thr366, Tyr367, Ile368, Cys369, or Ala374 in the amino acid sequence shown in SEQ ID NO: 1 is replaced with another amino acid residue.

More preferably, the glucose dehydrogenase of the present invention has at least one mutation selected from the group consisting of Met365Trp, Met365Phe, Thr366Asn, Thr366Ile, Thr366Asp, Thr366Lys, Tyr367Asp, Ile368Asn, Cys369Arg, and Ala374Pro in the amino acid sequence shown in SEQ ID NO: 1.

In another aspect, the modified PQQGDH of the present invention has a mutation described above and also has another mutation in which Asp167 of the amino acid sequence of SEQ ID NO: 1 is replaced with another amino acid residue, especially by glutamic acid. Involvement of Asp167 in recognition and binding of a substrate by PQQGDH is described in Japanese Patent Public Disclosure No. 2001-346587. In general, however, no prediction can be made regarding the changes of substrate specificity and enzyme activity which may be caused by simultaneously altering the amino acid residues in the 4D5A loop domain and/or other domains. Therefore, it was a surprising discovery in the present invention that both improved specificity for glucose and high enzyme activity can be achieved at the same time by introducing double mutations.

In another aspect, the invention provides a glucose dehydrogenase having pyrroloquinolme quinone as a coenzyme comprising one of the sequences as follows:

```
Cys Gly Glu Xaa Thr Tyr Ile
(SEQ ID NO: 3)

(wherein Xaa is Met or Trp)

Gly Glu Met Xaa Tyr Ile Cys
(SEQ ID NO: 4)

(wherein Xaa is Asp, Lys, Ile or Asn)

Glu Met Thr Asp Ile Cys Trp
(SEQ ID NO: 5)

Met Thr Tyr Asp Cys Trp Pro
(SEQ ID NO: 6)

Thr Tyr Ile Arg Trp Pro Thr
(SEQ ID NO: 7)

and

Pro Thr Val Pro Pro Ser Ser.
(SEQ ID NO: 8)
```

The invention also provides a gene coding for PQQGDH of the invention, a vector and a transformant comprising the gene of the invention, a method for preparing PQQGDH of the invention, as well as a glucose assay kit and a glucose sensor comprising PQQGDH of the invention.

Since the enzyme PQQGDH of the invention shows a low level of substrate inhibition by glucose, it is useful for measuring the level of glucose even at high glucose concentrations.

DETAILED EXPLANATION OF THE INVENTION

Preparation Method of Modified PQQGDH

Figure 1:
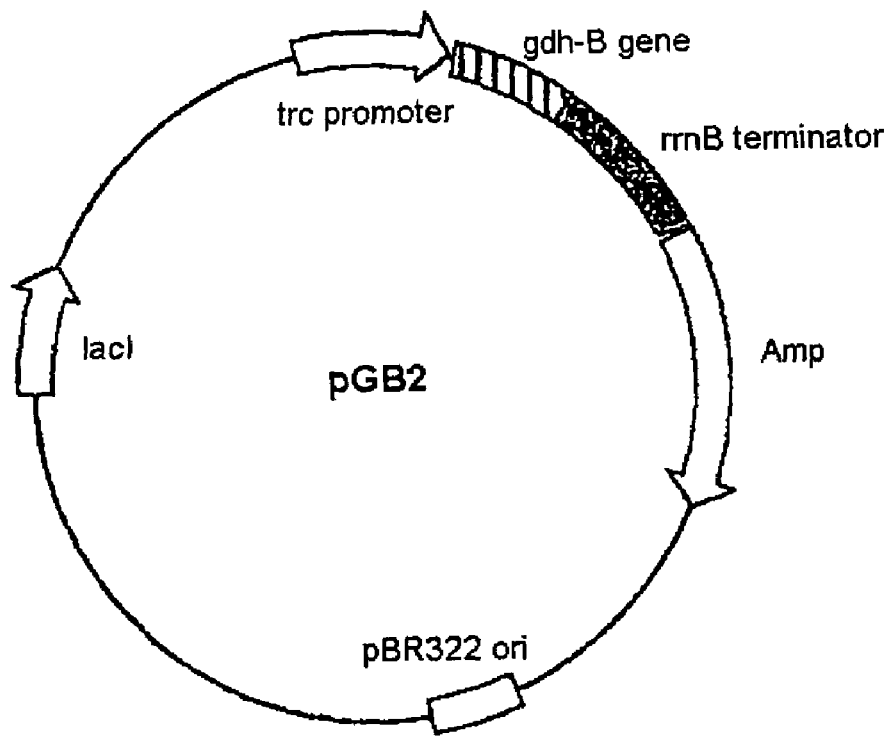
FIG. 1 shows construction of the pGB2 plasmid used in the invention.

The sequence of the gene encoding wild type water-soluble PQQGDH protein derived from *Acinetobacter calcoaceticus* are defined in SEQ ID NO:2.

Genes encoding modified PQQGDHs of the present invention can be constructed by replacing the nucleotide sequences encoding certain amino acids of the wild type water-soluble PQQGDH with the nucleotide sequences encoding the amino acids to be replaced. A wide range of methods for site-specific mutagenesis have been elaborated in the art. See, for example, Sambrook et al., "Molecular cloning; A Laboratory Manual", second edition, 1989, Cold Spring Harbor Laboratory Press, New York.

The mutant gene obtained in this manner is inserted into an expression vector (such as a plasmid) and transformed into an appropriate host (such as *E. coli*). A wide variety of host-vector systems have been developed in the art to express exogenous proteins. For example, bacteria, yeast, and cultured cells can be used as hosts.

As long as its glucose dehydrogenase activity is retained, the modified PQQGDH of the invention can further contain deletion, substitution or addition of other amino acid residues. A wide range of methods for site-specific mutagenesis are available in the art. See, for example, Sambrook et al., "Molecular cloning; A Laboratory Manual", second edition, 1989, Cold Spring Harbor Laboratory Press, New York.

Moreover, those skilled in the art can determine a region in a water-soluble PQQGDH derived from other bacteria which corresponds to the amino acid residues 349–377 of the water-soluble PQQGDH derived from *Acinetobacter calcoaceticus* by comparing the array of the primary structure of the proteins, or by comparing the secondary structures predicted from the primary structures of the enzymes. Thus, additional modified PQQGDHs with reduced substrate inhibition can be obtained by substituting amino acid residues in this region with another amino acid residues. Such modified PQQGDHs are also within the scope of the present invention.

After culturing the transformants expressing modified PQQGDH, obtained as described above, the cells may be collected by centrifugation and then crushed by French press, or the periplasmic enzymes may be released into the culture by osmotic shock. After ultracentrifugation, soluble fractions containing PQQGDH can be obtained. Alternatively, expressed PQQGDH can be secreted into the culture by using an appropriate host-vector system.

The soluble fraction obtained as described above is then purified by cation exchange chromatography. Purification can be performed by following the general instructions described in the textbooks known in the art. A wide variety of columns for cation exchange chromatography are available for protein purification, and any of them can be utilized in this invention, including CM-5PW, CM-Toyopearl 650M, SP-5PW (Toso Co.), and S-Sepharose, Mono-S, S-Resource (Pharmacia Corp.). The column is equilibrated with an appropriate buffer, the sample is applied to the column, and then the unabsorbed materials are washed away. Suitable buffers are, for example, phosphate buffer or MOPS buffer.

Then, substances absorbed in the column can be eluted by applying a buffer containing a higher salt concentration. The concentration of salt can be changed gradually or linearly or combination thereof by using buffers containing different salt concentrations. Elution of the sample is monitored by absorptiometer and the solution is fractionated into appropriate volumes. Enzyme activity is measured for each fraction, and the desired fractions are collected to obtain a purified preparation of the modified enzyme of the invention.

In addition, conventional methods known in the art, such as filtration, dialysis, gel filtration chromatography, or affinity chromatography, can be used before or after cation exchange chromatography, if necessary.

Measurement of Enzyme Activity

The PQQGDH of the present invention with coenzyme PQQ catalyzes oxidation of glucose to produce gluconolactone. The enzyme activity can be quantified by color-developing reaction of a redox dye to measure the amount of PQQ reduced with glucose oxidation by PQQGDH. Example of color-developing reagents include PMS (Phenazine methosulfate), DCIP (2,6-dichlorophenolindophenol), potassium ferricyanide, and ferrocene.

Evaluation of Substrate Inhibition

The degree of substrate inhibition of the PQQGDH of the present invention can be evaluated by its inhibition constant (Ksi). Ksi is represented by the higher one of the substrate concentrations which show half of the highest level of the enzyme activity, when the enzyme activity is measured using various glucose concentrations.

Evaluation of Substrate Specificity

The glucose specificity of the present invention can be evaluated by measuring relative enzyme activity with respect to the activity for glucose, as described above, by using a variety of sugars such as 2-deoxy-D-glucose, mannose, allose, 3-o-methyl-D-glucose, galactose, xylose, lactose, and maltose as a substrate.

Glucose Assay Kit

The present invention also provides a glucose assay kit containing the modified PQQGDH of the invention. The glucose assay kit of the invention may contain a sufficient quantity of the modified PQQGDH to carry out at least one assay. Besides modified PQQGDH, the kit may typically comprise buffers required for assay, a mediator, a standard solution of glucose to generate a calibration curve, and instructions for use. The modified PQQGDH can be supplied in a variety of forms, for example, as freeze-dried reagent or appropriate stock solutions. Preferably, the modified PQQGDH of the present invention may be supplied in the form of a holoenzyme, but can be supplied in the form of apoenzyme and converted into a holoenzyme before use.

Glucose Sensor

The present invention also provides a glucose sensor containing the modified PQQGDH of the invention. Carbon, gold, or platinum may be used as an electrode, and the enzyme of the present invention is immobilized on the electrode. Immobilization methods includes, for example, methods using cross-linking reagents, inclusion into a macromolecular matrix, coating with dialysis membrane, methods using photo-crosslinking polymer, electric conductive polymer, and redox polymer. The enzyme can also be immobilized in a polymer or adsorbed on the electrode together with an electron mediator, such as ferrocene or its derivative. Combinations of the above may also be used. Preferably, the modified PQQGDH of the present invention is immobilized on the electrode in the form of a holoenzyme, but can also be immobilized in the form of apoenzyme and PQQ is supplied as another layer or in solution. Typically, the modified PQQGDH of the present invention is immobilized on the electrode using glutaraldehyde, then free functional moieties of glutaraldehyde are blocked by treatment with a reagent having amine groups.

Measurement of glucose concentration is carried out as described below. Buffer, PQQ, $CaCl_2$, and a mediator are placed into a constant-temperature cell and are kept at a constant temperature. Potassium ferricyanide and phenazine methosulfate may be used as a mediator. An electrode in which the modified PQQGDH of the present invention is immobilized are used as a working electrode, together with a counter electrode (e.g., platinum) and a reference electrode (e.g., Ag/AgCl electrode). A constant voltage is applied to the carbon electrode. After the current reaches a constant value, a glucose-containing sample is added and the increase in the current is measured. The glucose concentration in the sample can be calculated using a calibration curve generated by standard concentration glucose solutions.

All patents and references cited in this specification are incorporated by reference. All the contents disclosed in the specifications and drawings of Japanese Patent Application Nos. 2003-71744 and 2002-172955, on which the application claims priority, are incorporated herein by reference.

The working examples described below further illustrate the invention without limiting the present invention.

EXAMPLE 1

Construction of Gene Encoding Modified PQQGDH Enzyme

Figure 2:
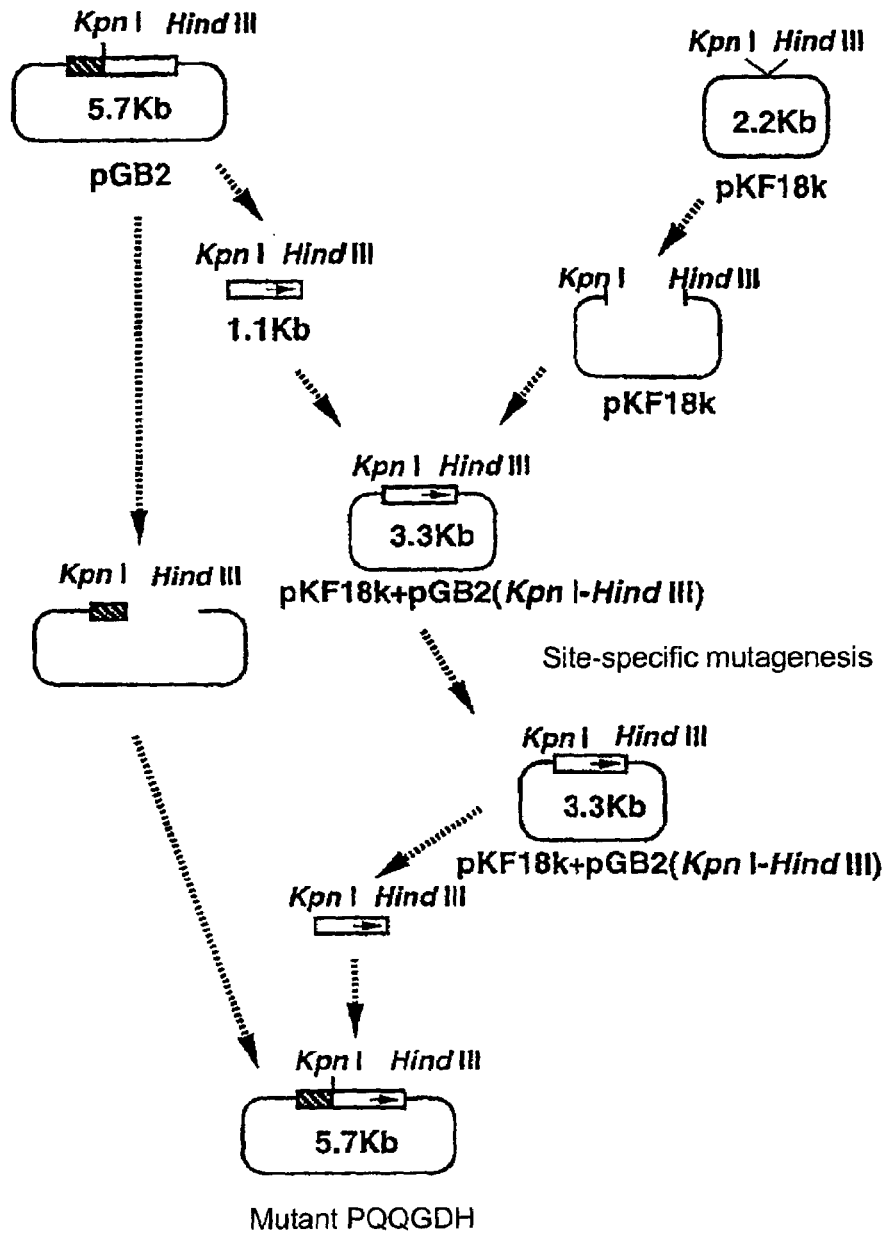
FIG. 2 shows a method of constructing a mutant coding for the modified enzyme of the invention.
Figure 3:
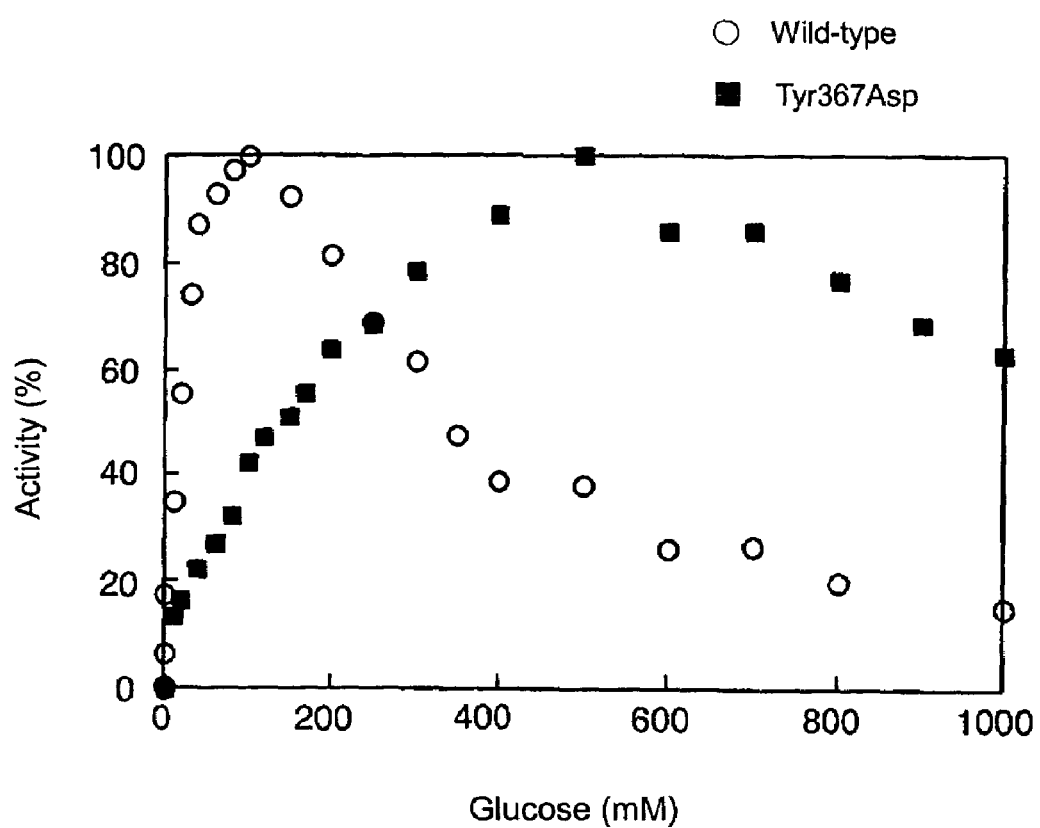
FIG. 3 shows the SV plot of the modified enzyme Tyr367Asp of the invention.
Figure 4:
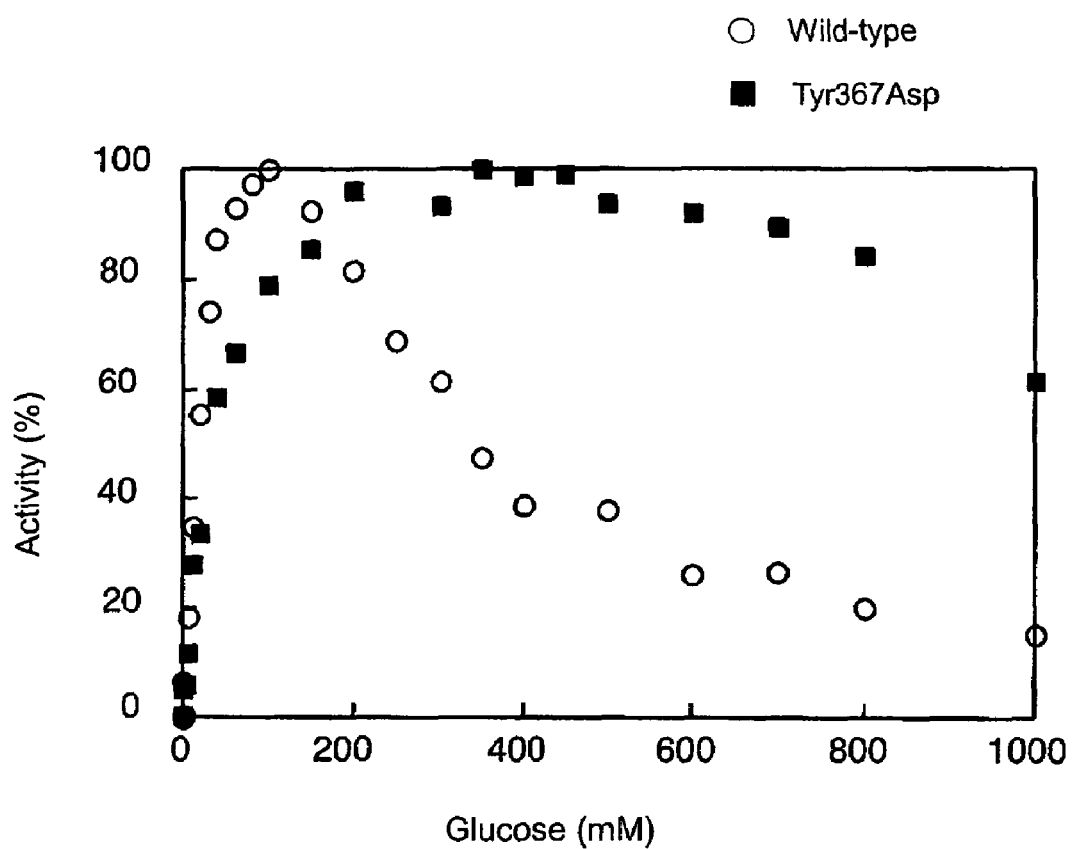
FIG. 4 shows the SV plot of the modified enzyme Cys369Arg of the invention.

Mutagenesis was carried out based on the structural gene of PQQGDH derived from Acinetobacter calcoaceticus (SEQ ID NO:2). pGB2 plasmid was constructed by inserting the structural gene of PQQGDH derived from Acinetobacter calcoaceticus into the multi-cloning site of pTrc99A vector (Pharmacia) (FIG. 1). Wild type gene sequence encoding PQQGDH was replaced with altered gene sequence encoding modified PQQGDH by standard method as previously described. Site specific mutagenesis was performed using the pGB2 plasmid as shown in FIG. 2. The sequences of synthetic oligonucleotides used for mutagenesis are shown below. In order to construct a mutant containing two mutations, two oligonucleotide primers were used simultaneously for mutagenesis.

```
Met365Trp
3'-GT TGA ACA CCT CTC CCA TGG ATG TAA AC-5'
(SEQ ID NO: 9)

Met365Phe
3'-GT TGA ACA CCT CTC CCT TGG ATG TAA AC-5'
(SEQ ID NO: 10)

Thr366Asn
3'-GGT TGA ACA CCT CTC TAC TTG ATG TAA ACG AC-5'
(SEQ ID NO: 11)

Thr366Ile
3'-GGT TGA ACA CCT CTC TAC TAG ATG TAA ACG AC-5'
(SEQ ID NO: 12)

Thr366Asp
3'-GA ACA CCT CTC TAC CTG ATG TAA ACG ACC G-5'
(SEQ ID NO: 13)

Thr366Lys
3'-GA ACA CCT CTC TAC TTT ATG TAA ACG ACC G-5'
(SEQ ID NO: 14)
```

-continued

Tyr367Asp
3'-GGT TGA ACA CCT CTC TAC TGG CTG TAA ACG ACC-5'
(SEQ ID NO: 15)

Ile368Asn
3'-AC TGG ATG TTA ACG ACC GG-5'
(SEQ ID NO: 16)

Cys369Arg
3'-GG ATG TAA ACG ACC GGT TGT C-5'
(SEQ ID NO: 17)

Ala374Pro
3'-C GGT TGT CAA GGT GGC AGT AGA CG-5'
(SEQ ID NO: 18)

Asp167Glu
3'-GGA AGT AGT TTT CTT GTA GTC AGT CC-5'
(SEQ ID NO: 19)

A template was prepared by inserting the KpnI-HindIII fragment containing part of the gene encoding PQQGDH derived from *Acinetobacter calcoaceticus* into pKF18k vector plasmid (TaKaRa). A mixture of template (50 fmol), selection primer (5 pmol) supplied in Mutan-Express Km kit, phosphorylated target primer (50 pmol), and the annealing buffer supplied in the kit (1/10 of total volume (20 μl)) was prepared, and plasmid DNA was denatured to single-strand by heating at 100° C. for 3 minutes. The selection primer was designed for the reversion of double-amber mutation on the Kanamycin resistance gene of the pKF18k plasmid. Plasmid DNA was put on ice for 5 minutes for annealing of the primers. A complementary strand was synthesized by adding the following reagents: 3 μl of extension buffer supplied in the kit, 1 μl of T4 DNA ligase, 1 μl of T4 DNA polymerase, and 5 μl of sterilized water. *E. coli* BMH71–18mutS, a DNA mismatch repair deficient strain, was transformed with the synthesized DNA and cultured overnight with vigorous shaking to amplify the plasmid.

Then, each plasmid was extracted from bacteria and transformed into *E. coli* MV1184, and the plasmid was extracted from the colonies. The sequence of the plasmid was determined to confirm successful introduction of the desired mutations. Kpn I-Hind III gene fragment encoding wild type PQQGDH on pGB2 plasmid was replaced with the fragment containing the mutation to construct a series of mutated PQQGDH genes.

EXAMPLE 2

Preparation of Modified Enzyme

A Gene encoding wild type or modified PQQGDH was inserted into the multi-cloning site of pTrc99A (Pharmacia), and the constructed plasmid was transformed into *E. coli* DH5α. Transformants were cultured in 450 ml of L-broth using a Sakaguchi flask at 37° C. with vigorous shaking, and then inoculated in 7 L of L-broth containing 1 mM $CaCl_2$ and 500 μM PQQ. After three hours of cultivation, IPTG was added to a final concentration of 0.3 mM, and cultivation was continued for another 1.5 hours. The culture medium was centrifuged (5000 xg, 10 min, 4° C.), and the pellet was washed with 0.85% NaCl twice. The cells were resuspended in 10 mM phosphate buffer (pH7.0), crushed with French press (110 MPa), and centrifuged twice to remove the debris. The supernatant was ultracentrifuged (40,000 rpm, 90 min, 4° C.), and the supernatant was collected as a water-soluble fraction. This fraction was dialyzed against A buffer (10 mM MOPS-NaCl buffer (pH 7.0)) at 4° C. overnight to obtain a crude preparation.

EXAMPLE 3

Measurement of Enzyme Activity

Enzyme activity was measured in MOPS-NaOH buffer (pH7.0) containing PMS (phenazine methosulfate)-DCIP (2,6-dichlorophenolindophenol). Changes in absorbance of DCIP was recorded with a spectrophotometer at 600 nm, and the reduction rate of absorbance was defined as the reaction rate of the enzyme. In this measurement, enzyme activity which reduced 1 μmol of DCIP in one minute was regarded as 1 unit. The molar absorption coefficient of DCIP at pH 7.0 was 16.3 $M^{-1}$.

EXAMPLE 4

Evaluation of Substrate Inhibition

Each of the crude enzyme preparation of wild type PQQGDH and modified PQQGDHs obtained in Example 3 was converted to a holoenzyme in the presence of 1 μM PQQ and 1 mM $CaCl_2$ for 1 hour or more in the same manner as described above. The solution was divided into aliquots of 187 μl each, and mixed with 3 μl of activation reagents (6 mM DCIPA 48 μl, 600 mM PMS 8 μl, 10 mM phosphate buffer pH 7.0 16 μl) and 10 μl of D-glucose of various concentrations. Enzyme activity was measured at room temperature as described above. Enzyme activity was plotted against substrate concentration, and Km, Vmax, and Ksi values were determined. The results are shown in FIG. 1. The SV plot for Tyr367Asp and SV plot for Cys369Arg are shown in Table 3 and Table 4, respectively. These results clearly demonstrated that modified PQQGDH of the invention showed a higher Ksi value than wild type PQQGDH and significant reduction in substrate inhibition.

TABLE 1

| | Km (mM) | Vmax (U/mg protein) | Ksi (mM) | Ksi/Km |
|---|---|---|---|---|
| Wild type | 23 | 154 | 196 | 8 |
| Met365Phe | 36 | 619 | 394 | 10 |
| Met365Trp | 38 | 89 | 458 | 12 |
| Thr366Asn | 32 | 300 | 500 | 15 |
| Thr366Ile | 39 | 87 | 228 | 6 |
| Thr366Asp | 35 | 196 | 556 | 16 |
| Thr366Lys | 23 | 300 | 202 | 9 |
| Tyr367Asp | 280 | 11 | 830 | 3 |
| Ile368Asn | 61 | 60 | 535 | 9 |
| Cys369Arg | 65 | 6 | 1402 | 22 |
| Ala374Pro | n.d. | 2 | 250 | n.d. |

EXAMPLE 5

Purification of Enzyme

The crude enzyme preparation obtained in Example 2 was adsorbed in a cation exchange chromatography column filled with TSKgel CM-TOYOPEARL 650M (Toso Co.). The column was washed with 750 ml of 10 mM phosphate buffer pH 7.0 and the enzyme was eluted with 10 mM phosphate buffer pH 7.0 containing from 0 M to 0.2 M NaCl. The flow rate was 5 mL/min. Fractions showing GDH activity were collected and dialyzed against 10 mM MOPS-NaOH buffer (pH 7.0) overnight. In this manner, modified PQQGDH protein was purified which exhibited a single band under electrophoresis. Enzyme activity and substrate inhibition of the purified enzyme were measured in the presence of 0.6 mM PMS. The results are shown in Table 2. The modified enzymes, Thr366Asn and Thr366Asp, of the invention showed enzyme activity comparable to or higher than the wild type as well as a higher Ksi value.

TABLE 2

|  | Km (mM) | Vmax (U/mg protein) | kcat (sec$^{-1}$) | kcat/Km (mM$^{-1}$ · sec$^{-1}$) | Ksi (mM) | Ksi/Km |
| --- | --- | --- | --- | --- | --- | --- |
| Wild type | 27 | 8899 | 7451 | 276 | 250 | 9 |
| Thr366Asn | 14 | 10158 | 8505 | 608 | 522 | 37 |
| Thr366Asp | 28 | 5166 | 4283 | 153 | 332 | 12 |

EXAMPLE 6

Construction of Enzyme with Double Mutations

An enzyme with double mutations Asp167Glu/Thr366Asn was constructed and its characteristics were examined. Modified enzyme with Asp167Glu mutation is known to have a higher substrate specificity to glucose. Substrate inhibition of the enzyme with double mutations was determined in the same manner as Example 5 and the results were as follows: Ksi=600 mM, Km=26 mM, and Ksi/Km=23. These values were equivalent to those of the modified enzyme of the invention as indicated in Example 5 and were higher than those of the wild type enzyme.

Then, the substrate specificity of this enzyme was examined. Crude enzyme preparations of the wild type and the modified PQQGDHs obtained in Example 2 were converted into a holoenzyme in the presence of 1 μM PQQ, 1 mM CaCl$_2$ for one hour or more. This solution was divided into aliquots or 187 μl, and mixed with 3 μl of activation reagent containing electron acceptor (6 mM DCIP, 600 mM PMS, 10 mM phosphate buffer pH 7.0), and substrate were added (final concentration: 0.06 mM DCIP, 0.6 mM PMS). Ten μl of glucose, lactose or maltose was added as a substrate to a final concentration of 100 mM and the samples were incubated for 30 minutes at room temperature. The enzyme activity was measured in the same manner as Example 3. The values were expressed as a relative activity to the activity for glucose (100). The results are shown in Table 3. Modified enzyme with double mutations, Thr366Asn and Asp167Glu, exhibited higher substrate specificity to glucose than either wild type or modified enzyme with a single mutation Asp167Glu. In addition, modified enzyme with single mutation Thr366Asn has an equivalent level of substrate specificity to that of the wild type enzyme (data not shown).

TABLE 3

|  | Glucose | Lactose | Maltose |
| --- | --- | --- | --- |
| Wild type | 100% | 54% | 58% |
| Asp167Glu | 100% | 32% | 10% |
| Asp167Glu/Thr366Asn | 100% | 20% |  |

In addition, the enzyme activity of this double mutant was measured in the presence of 0.06 mM DCIP as electron acceptor and 10 mM glucose as substrate in the same manner as in Example 4. The modified enzyme with double mutations Thr366Asn and Asp167Glu exhibited higher enzyme activity than the wild type enzyme.

TABLE 4

| Wild type | 100% |
| --- | --- |
| Thr366Asn | 126% |
| Asp167Glu | 54% |
| Asp167Glu/Thr366Asn | 291% |

EXAMPLE 7

Preparation of Enzyme Sensor and its Evaluation

Twenty mg of carbon paste was added to 5 units of the modified enzyme and freeze-dried. The mixture was applied on the surface of a carbon paste electrode filled with approximately 40 mg of carbon paste, and the electrode was polished on a filter paper. This electrode was treated with MOPS buffer (pH 7.0) containing 1% glutaraldehyde for 30 minutes at room temperature and then treated with MOPS buffer (pH 7.0) containing 20 mM lysine for 20 minutes at room temperature to block unreacted glutaraldehyde. The electrode was equilibrated in 10 mM MOPS buffer (pH 7.0) for one hour or more at room temperature, then stored at 4° C.

The glucose concentration was measured using the glucose sensor thus prepared. Glucose concentration was quantified in the range from 5 mM to 50 mM by using the glucose sensor prepared with the modified PQQGDH of the invention.

INDUSTRIAL APPLICABILITY

The modified water-soluble PQQGDH of the present invention can be utilized for glucose measurement in the presence of high concentrations of glucose because of its low substrate inhibition.

The invention claimed is:

1. A modified glucose dehydrogenase composition comprising water-soluble *Acinetobacter calcoaceticus* pyrroloquinoline quinone glucose dehydrogenase having (PQQ) as as a coenzyme, wherein amino acid Thr342 or both the amino acid THr342 and amino acid Asp 143 of SEQ ID NO: 1 of the PQQGDH are replaced with other amino acid residues, and wherein said PQQGDH has an inhibition constant (Ksi) of 200 mM or more.

2. The modified glucose dehydrogenase according to claim 1, wherein Thr342 of the amino acid sequence defined in SEQ ID NO: 1 of PQQGDH is replaced with another amino acid.

3. The modified glucose dehydrogenase according to claim 1, wherein Thr342 of the amino acid sequence defined in SEQ ID NO: 1 of PQQGDH is replaced with aspartic acid, lysine, isoleucine, or asparagine.

4. The modified glucose dehydrogenase according to claim 1, wherein the amino acid residue Thr342 of the amino acid sequence defined in SEQ ID NO: 1 of PQQGDH is replaced with another amino acid and wherein Asp 143 of SEQ ID NO: 1 is replaced with glutamic acid.

5. A The modified glucose dehydrogenase according to claim 1, wherein Thr342 of the amino acid sequence defined in SEQ ID NO: 1 of PQQGDH is replaced with aspartic acid, lysine, isoleucine, or asparagine, and wherein Asp143 of SEQ ID NO: 1 is replaced with glutamic acid.

6. A glucose assay kit comprising the modified glucose dehydrogenase according to claim 1.

7. A glucose sensor comprising the modified glucose dehydrogenase according to claim 1.

* * * * *

SEQUENCE LISTING

<160> NUMBER OF SEQ ID NOS: 19

<210> SEQ ID NO 1
<211> LENGTH: 454
<212> TYPE: PRT
<213> ORGANISM: Acinetobacter calcoaceticus

<400> SEQUENCE: 1

-continued

```
Asp Val Pro Leu Thr Pro Ser Gln Phe Ala Lys Ala Lys Ser Glu Asn
 1               5                  10                  15

Phe Asp Lys Lys Val Ile Leu Ser Asn Leu Asn Lys Pro His Ala Leu
             20                  25                  30

Leu Trp Gly Pro Asp Asn Gln Ile Trp Leu Thr Glu Arg Ala Thr Gly
             35                  40                  45

Lys Ile Leu Arg Val Asn Pro Glu Ser Gly Ser Val Lys Thr Val Phe
 50                  55                  60

Gln Val Pro Glu Ile Val Asn Asp Ala Asp Gly Gln Asn Gly Leu Leu
 65                  70                  75                  80

Gly Phe Ala Phe His Pro Asp Phe Lys Asn Asn Pro Tyr Ile Tyr Ile
             85                  90                  95

Ser Gly Thr Phe Lys Asn Pro Lys Ser Thr Asp Lys Glu Leu Pro Asn
             100                 105                 110

Gln Thr Ile Ile Arg Arg Tyr Thr Tyr Asn Lys Ser Thr Asp Thr Leu
             115                 120                 125

Glu Lys Pro Val Asp Leu Leu Ala Gly Leu Pro Ser Ser Lys Asp His
             130                 135                 140

Gln Ser Gly Arg Leu Val Ile Gly Pro Asp Gln Lys Ile Tyr Tyr Thr
145                 150                 155                 160

Ile Gly Asp Gln Gly Arg Asn Gln Leu Ala Tyr Leu Phe Leu Pro Asn
                 165                 170                 175

Gln Ala Gln His Thr Pro Thr Gln Gln Glu Leu Asn Gly Lys Asp Tyr
                 180                 185                 190

His Thr Tyr Met Gly Lys Val Leu Arg Leu Asn Leu Asp Gly Ser Ile
                 195                 200                 205

Pro Lys Asp Asn Pro Ser Phe Asn Gly Val Val Ser His Ile Tyr Thr
                 210                 215                 220

Leu Gly His Arg Asn Pro Gln Gly Leu Ala Phe Thr Pro Asn Gly Lys
225                 230                 235                 240

Leu Leu Gln Ser Glu Gln Gly Pro Asn Ser Asp Asp Glu Ile Asn Leu
                 245                 250                 255

Ile Val Lys Gly Gly Asn Tyr Gly Trp Pro Asn Val Ala Gly Tyr Lys
                 260                 265                 270

Asp Asp Ser Gly Tyr Ala Tyr Ala Asn Tyr Ser Ala Ala Ala Asn Lys
                 275                 280                 285

Ser Ile Lys Asp Leu Ala Gln Asn Gly Val Lys Val Ala Ala Gly Val
                 290                 295                 300

Pro Val Thr Lys Glu Ser Glu Trp Thr Gly Lys Asn Phe Val Pro Pro
305                 310                 315                 320

Leu Lys Thr Leu Tyr Thr Val Gln Asp Thr Tyr Asn Tyr Asn Asp Pro
                 325                 330                 335

Thr Cys Gly Glu Met Thr Tyr Ile Cys Trp Pro Thr Val Ala Pro Ser
                 340                 345                 350

Ser Ala Tyr Val Tyr Lys Gly Gly Lys Lys Ala Ile Thr Gly Trp Glu
                 355                 360                 365

Asn Thr Leu Leu Val Pro Ser Leu Lys Arg Gly Val Ile Phe Arg Ile
                 370                 375                 380

Lys Leu Asp Pro Thr Tyr Ser Thr Thr Tyr Asp Asp Ala Val Pro Met
385                 390                 395                 400

Phe Lys Ser Asn Asn Arg Tyr Arg Asp Val Ile Ala Ser Pro Asp Gly
                 405                 410                 415

Asn Val Leu Tyr Val Leu Thr Asp Thr Ala Gly Asn Val Gln Lys Asp
```

420             425             430
Asp Gly Ser Val Thr Asn Thr Leu Glu Asn Pro Gly Ser Leu Ile Lys
        435                 440                 445

Phe Thr Tyr Lys Ala Lys
    450

<210> SEQ ID NO 2
<211> LENGTH: 1612
<212> TYPE: DNA
<213> ORGANISM: Acinetobacter calcoaceticus

<400> SEQUENCE: 2

```
agctactttt atgcaacaga gcctttcaga aatttagatt ttaatagatt cgttattcat    60
cataatacaa atcatataga gaactcgtac aaacccttta ttagaggttt aaaaattctc   120
ggaaaatttt gacaatttat aaggtggaca catgaataaa catttattgg ctaaaattgc   180
tttattaagc gctgttcagc tagttacact ctcagcattt gctgatgttc ctctaactcc   240
atctcaattt gctaaagcga atcagagaa ctttgacaag aaagttattc tatctaatct   300
aaataagccg catgctttgt tatggggacc agataatcaa atttggttaa ctgagcgagc   360
aacaggtaag attctaagag ttaatccaga gtcgggtagt gtaaaaacag ttttcaggt    420
accagagatt gtcaatgatg ctgatgggca gaatggttta ttaggttttg ccttccatcc   480
tgattttaaa aataatcctt atatctatat ttcaggtaca tttaaaaatc gaaatctac    540
agataaagaa ttaccgaacc aaacgattat tcgtcgttat acctataata atcaacaga    600
tacgctcgag aagccagtcg atttattagc aggattacct tcatcaaaag accatcagtc   660
aggtcgtctt gtcattgggc cagatcaaaa gatttattat acgattggtg accaagggcg   720
taaccagctt gcttatttgt tcttgccaaa tcaagcacaa catacgccaa ctcaacaaga   780
actgaatggt aaagactatc acacctatat gggtaaagta ctacgcttaa atcttgatgg   840
aagtattcca aaggataatc caagttttaa cggggtggtt agccatattt atacacttgg   900
acatcgtaat ccgcagggct tagcattcac tccaaatggt aaattattgc agtctgaaca   960
aggcccaaac tctgacgatg aaattaacct cattgtcaaa ggtggcaatt atggttggcc  1020
gaatgtagca ggttataaag atgatagtgg ctatgcttat gcaaattatt cagcagcagc  1080
caataagtca attaaggatt tagctcaaaa tggagtaaaa gtagccgcag gggtccctgt  1140
gacgaaagaa tctgaatgga ctggtaaaaa ctttgtccca ccattaaaaa ctttatatac  1200
cgttcaagat acctacaact ataacgatcc aacttgtgga gagatgacct acatttgctg  1260
gccaacagtt gcaccgtcat ctgcctatgt ctataagggc ggtaaaaaag caattactgg  1320
ttgggaaaat acattattgg ttccatcttt aaaacgtggt gtcattttcc gtattaagtt  1380
agatccaact tatagcacta cttatgatga cgctgtaccg atgtttaaga gcaacaaccg  1440
ttatcgtgat gtgattgcaa gtccagatgg gaatgtctta tatgtattaa ctgatactgc  1500
cggaaatgtc caaaaagatg atggctcagt aacaaataca ttagaaaacc caggatctct  1560
cattaagttc acctataagg ctaagtaata cagtcgcatt aaaaaaccga tc          1612
```

<210> SEQ ID NO 3
<211> LENGTH: 7
<212> TYPE: PRT
<213> ORGANISM: Acinetobacter calcoaceticus
<220> FEATURE:
<221> NAME/KEY: misc_feature
<222> LOCATION: (4)..(4)
<223> OTHER INFORMATION: Xaa is Met or Trp

```
<400> SEQUENCE: 3

Cys Gly Glu Xaa Thr Tyr Ile

<210> SEQ ID NO 4
<211> LENGTH: 7
<212> TYPE: PRT
<213> ORGANISM: Acinetobacter calcoaceticus
<220> FEATURE:
<221> NAME/KEY: misc_feature
<222> LOCATION: (4)..(4)
<223> OTHER INFORMATION: Xaa is Asp, Lys, Ile or Asn

<400> SEQUENCE: 4

Gly Glu Met Xaa Tyr Ile Cys

<210> SEQ ID NO 5
<211> LENGTH: 7
<212> TYPE: PRT
<213> ORGANISM: Acinetobacter calcoaceticus

<400> SEQUENCE: 5

Glu Met Thr Asp Ile Cys Trp

<210> SEQ ID NO 6
<211> LENGTH: 7
<212> TYPE: PRT
<213> ORGANISM: Acinetobacter calcoaceticus

<400> SEQUENCE: 6

Met Thr Tyr Asp Cys Trp Pro

<210> SEQ ID NO 7
<211> LENGTH: 7
<212> TYPE: PRT
<213> ORGANISM: Acinetobacter calcoaceticus

<400> SEQUENCE: 7

Thr Tyr Ile Arg Trp Pro Thr

<210> SEQ ID NO 8
<211> LENGTH: 7
<212> TYPE: PRT
<213> ORGANISM: Acinetobacter calcoaceticus

<400> SEQUENCE: 8

Pro Thr Val Pro Pro Ser Ser

<210> SEQ ID NO 9
<211> LENGTH: 28
<212> TYPE: DNA
<213> ORGANISM: Artificial Sequence
<220> FEATURE:
<223> OTHER INFORMATION: synthetic oligonucleotide primer for point
      mutation

<400> SEQUENCE: 9
caaatgtagg taccctctcc acaagttg                                      28

<210> SEQ ID NO 10
<211> LENGTH: 28
<212> TYPE: DNA
<213> ORGANISM: Artificial Sequence
<220> FEATURE:
<223> OTHER INFORMATION: synthetic oligonucleotide primer for point
``` mutation

<400> SEQUENCE: 10
caaatgtagg ttccctctcc acaagttg                                    28

<210> SEQ ID NO 11
<211> LENGTH: 32
<212> TYPE: DNA
<213> ORGANISM: Artificial Sequence
<220> FEATURE:
<223> OTHER INFORMATION: synthetic oligonucleotide primer for point
      mutation

<400> SEQUENCE: 11
cagcaaatgt agttcatctc tccacaagtt gg                               32

<210> SEQ ID NO 12
<211> LENGTH: 32
<212> TYPE: DNA
<213> ORGANISM: Artificial Sequence
<220> FEATURE:
<223> OTHER INFORMATION: synthetic oligonucleotide primer for point
      mutation

<400> SEQUENCE: 12
cagcaaatgt agatcatctc tccacaagtt gg                               32

<210> SEQ ID NO 13
<211> LENGTH: 30
<212> TYPE: DNA
<213> ORGANISM: Artificial Sequence
<220> FEATURE:
<223> OTHER INFORMATION: synthetic oligonucleotide primer for point
      mutation

<400> SEQUENCE: 13
gccagcaaat gtagtccatc tctccacaag                                  30

<210> SEQ ID NO 14
<211> LENGTH: 30
<212> TYPE: DNA
<213> ORGANISM: Artificial Sequence
<220> FEATURE:
<223> OTHER INFORMATION: synthetic oligonucleotide primer for point
      mutation

<400> SEQUENCE: 14
gccagcaaat gtatttcatc tctccacaag                                  30

<210> SEQ ID NO 15
<211> LENGTH: 33
<212> TYPE: DNA
<213> ORGANISM: Artificial Sequence
<220> FEATURE:
<223> OTHER INFORMATION: synthetic oligonucleotide primer for point
      mutation

<400> SEQUENCE: 15
ccagcaaatg tcggtcatct ctccacaagt tgg                              33

<210> SEQ ID NO 16
<211> LENGTH: 19
<212> TYPE: DNA
<213> ORGANISM: Artificial Sequence
<220> FEATURE:
<223> OTHER INFORMATION: synthetic oligonucleotide primer for point
      mutation

```
<400> SEQUENCE: 16
ggccagcaat tgtaggtca                                                        19

<210> SEQ ID NO 17
<211> LENGTH: 21
<212> TYPE: DNA
<213> ORGANISM: Artificial Sequence
<220> FEATURE:
<223> OTHER INFORMATION: synthetic oligonucleotide primer for point
      mutation

<400> SEQUENCE: 17
ctgttggcca gcaaatgtag g                                                     21

<210> SEQ ID NO 18
<211> LENGTH: 24
<212> TYPE: DNA
<213> ORGANISM: Artificial Sequence
<220> FEATURE:
<223> OTHER INFORMATION: synthetic oligonucleotide primer for point
      mutation

<400> SEQUENCE: 18
gcagatgacg gtggaactgt tggc                                                  24

<210> SEQ ID NO 19
<211> LENGTH: 26
<212> TYPE: DNA
<213> ORGANISM: Artificial Sequence
<220> FEATURE:
<223> OTHER INFORMATION: synthetic oligonucleotide primer for point
      mutation

<400> SEQUENCE: 19
cctgactgat gttcttttga tgaagg                                                26
```